United States Patent [19]

Hekker et al.

[11] Patent Number: 5,078,501
[45] Date of Patent: Jan. 7, 1992

[54] METHOD AND APPARATUS FOR OPTICALLY EVALUATING THE CONFORMANCE OF UNKNOWN OBJECTS TO PREDETERMINED CHARACTERISTICS

[75] Inventors: Roeland M. T. Hekker; Izhak M. Livny; Terence M. Haran; Robert D. Buck, all of Fairfield, Iowa

[73] Assignee: E. I. Du Pont de Nemours and Company, Wilmington, Del.

[21] Appl. No.: 476,130

[22] Filed: Feb. 5, 1990

Related U.S. Application Data

[63] Continuation of Ser. No. 137,417, Dec. 23, 1987, abandoned, which is a continuation-in-part of Ser. No. 920,513, Oct. 17, 1986, abandoned.

[51] Int. Cl.$^5$ .................. G02B 27/46; G06K 9/00
[52] U.S. Cl. ................... 359/561; 364/822; 382/31
[58] Field of Search ............ 364/822; 350/162.12, 350/162.13, 162.14; 382/2, 4, 31, 39, 50; 250/550

[56] References Cited

U.S. PATENT DOCUMENTS

| | | | |
|---|---|---|---|
| 2,798,605 | 7/1957 | Richards | 209/111 |
| 3,064,519 | 11/1962 | Shelton, Jr. | 88/1 |
| 3,305,834 | 2/1967 | Cooper et al. | 340/146.3 |
| 3,435,244 | 3/1969 | Burckhardt et al. | 250/219 |
| 3,450,889 | 6/1969 | Baker | 250/219 |
| 3,483,513 | 12/1969 | Burckhardt et al. | 340/146.3 |
| 3,497,704 | 2/1970 | Holmes et al. | 250/233 |
| 3,532,426 | 10/1970 | Lemmond | 356/71 |
| 3,536,376 | 10/1970 | Henning | 350/161 |
| 3,543,237 | 11/1970 | Cutler et al. | 340/146.3 |
| 3,549,800 | 12/1970 | Baker | 178/7.3 |
| 3,550,084 | 12/1970 | Bigelow et al. | 340/146.3 |
| 3,566,137 | 2/1971 | Lemmond | 250/219 |
| 3,581,280 | 5/1971 | Holeman | 340/146.3 F |
| 3,604,806 | 9/1971 | Redmann | 356/71 |
| 3,622,988 | 11/1971 | Caulfeld | 340/146.3 P |
| 3,633,035 | 1/1972 | Uchida et al. | 250/199 |
| 3,634,695 | 1/1972 | Barringer | 250/219 |
| 3,636,512 | 1/1972 | Edwards | 340/146.3 |
| 3,689,697 | 3/1972 | Kawasaki | 340/146.3 P |
| 3,689,772 | 9/1972 | George et al. | 250/211 |
| 3,694,657 | 9/1972 | Brooks | 250/216 |
| 3,697,149 | 10/1972 | Van Heeckeren et al. | 350/3.5 |
| 3,726,997 | 4/1973 | Gnau et al. | 178/6.8 |
| 3,735,374 | 5/1973 | Rembault | 340/213 |
| 3,737,856 | 6/1973 | Lehrer et al. | 340/146.3 Q |
| 3,744,879 | 7/1973 | Beard et al. | 350/162 |
| 3,764,979 | 10/1973 | Gabor | 340/146.3 |
| 3,776,616 | 12/1973 | Douklias | 350/162 |
| 3,778,166 | 12/1973 | Pease et al. | 356/71 |
| 3,779,492 | 12/1973 | Grumet | 244/3.17 |
| 3,781,113 | 12/1973 | Thomas | 356/71 |
| 3,788,749 | 1/1974 | George | 356/239 |
| 3,809,478 | 5/1974 | Talbot | 356/71 |
| 3,809,873 | 5/1974 | Klahr | 235/181 |
| 3,814,520 | 6/1974 | Baker et al. | 256/71 |
| 3,814,943 | 6/1974 | Baker et al. | 250/550 |
| 3,834,786 | 9/1974 | Carlsen | 250/3.5 |
| 3,853,403 | 12/1974 | Bentley | 356/71 |
| 3,869,697 | 3/1975 | Kawasaki | 350/162.12 |
| 3,872,293 | 3/1975 | Green | 235/181 |
| 3,891,968 | 6/1975 | McMahon | 340/146.3 |
| 3,905,019 | 9/1975 | Aoki et al. | 340/146.3 |
| 3,944,978 | 3/1976 | Jensen et al. | 340/146.3 E |
| 3,947,123 | 3/1976 | Carlson et al. | 356/39 |
| 3,972,616 | 8/1976 | Minami et al. | 356/71 |
| 3,984,802 | 10/1976 | Lippel, Jr. et al. | 340/5 H |
| 4,016,413 | 4/1977 | Bramley | 235/181 |
| 4,017,721 | 4/1977 | Michaud | 235/151.3 |
| 4,052,600 | 10/1977 | Wertheimer | 364/554 |
| 4,054,878 | 10/1977 | Diehl | 343/11 R |
| 4,063,799 | 12/1977 | Bernstein et al. | 350/162 SF |
| 4,067,645 | 1/1978 | Carlson et al. | 350/162 |
| 4,070,113 | 1/1978 | Frazer et al. | 356/104 |
| 4,084,255 | 4/1978 | Casasent et al. | 364/822 |
| 4,107,701 | 8/1978 | Sprague et al. | 346/108 |
| 4,110,116 | 8/1978 | Berg et al. | 350/358 |
| 4,118,099 | 10/1978 | Weiss et al. | 350/3.73 |
| 4,118,107 | 10/1978 | Parrent, Jr. et al. | 350/162 |
| 4,139,303 | 2/1979 | Carlson et al. | 382/43 |
| 4,150,360 | 4/1979 | Kopp et al. | 250/550 |
| 4,153,335 | 5/1979 | Buchan | 350/150 |
| 4,153,336 | 5/1979 | Manami et al. | 350/162 |
| 4,173,441 | 11/1979 | Wolf | 356/431 |
| 4,174,179 | 11/1979 | Tsuchudi et al. | 356/71 |
| 4,174,885 | 11/1979 | Joseph et al. | 350/162 |
| 4,187,000 | 2/1980 | Constant | 350/162 SF |
| 4,198,125 | 4/1980 | Tatian et al. | 350/162 SF |
| 4,277,137 | 7/1981 | Upatnieks et al. | 350/162 |
| 4,282,511 | 8/1981 | Southgate et al. | 340/146.3 F |

| | | | |
|---|---|---|---|
| 4,299,443 | 11/1981 | Minami et al. | 350/162 |
| 4,322,163 | 3/1982 | Schiller | 356/71 |
| 4,330,775 | 5/1982 | Iwamoto et al. | 340/146.3 |
| 4,340,300 | 7/1982 | Ruell | 356/71 |
| 4,357,676 | 11/1982 | Brown | 364/822 |
| 4,360,799 | 11/1982 | Leighty et al. | 350/162 SF |
| 4,370,024 | 1/1983 | Task et al. | 350/162.12 |
| 4,378,495 | 3/1983 | Miller | 250/223 |
| 4,383,734 | 5/1983 | Huignard et al. | 350/162.13 |
| 4,387,989 | 6/1983 | Pirich | 356/71 |
| 4,389,093 | 6/1983 | Jackson | 350/162.14 |
| 4,403,294 | 9/1983 | Hamada et al. | 364/507 |
| 4,414,566 | 11/1983 | Peyton et al. | 358/101 |
| 4,433,385 | 2/1984 | De Gasperi et al. | 364/554 |
| 4,445,141 | 4/1984 | Benton et al. | 358/294 |
| 4,449,144 | 5/1984 | Suzuki | 358/105 |
| 4,462,046 | 7/1984 | Spight | 358/101 |
| 4,477,829 | 10/1984 | Ziman et al. | 358/1 |
| 4,484,081 | 11/1984 | Cornyn, Jr. et al. | 250/563 |
| 4,490,849 | 12/1984 | Grumet et al. | 382/31 |
| 4,490,851 | 12/1984 | Gerhart et al. | 382/43 |
| 4,511,986 | 4/1985 | Bellar et al. | 364/576 |
| 4,513,441 | 4/1985 | Henshaw | 382/43 |
| 4,516,833 | 5/1985 | Fusek | 350/162.12 |
| 4,544,267 | 10/1985 | Schiller | 356/71 |
| 4,556,985 | 12/1985 | Hogno | 382/30 |
| 4,566,757 | 1/1986 | Fusek et al. | 350/162.12 |
| 4,573,197 | 2/1986 | Crimmins | 382/22 |
| 4,573,198 | 2/1986 | Anderson | 382/31 |
| 4,588,293 | 5/1986 | Axelrod | 356/239 |
| 4,624,367 | 11/1986 | Shafer et al. | 209/577 |
| 4,637,055 | 1/1987 | Taylor | 382/31 |
| 4,637,056 | 1/1987 | Sherman et al. | 382/31 |

OTHER PUBLICATIONS

Complex Spatial Filters for Image Deconvolution, *Proceedings of the IEEE,* vol. 65, No. 1, Jan. 1977.
Digitally Controlled Fourier Plane Filter, D. Casasent, Hybrid Processors, pp. 202, 203, 204, 232, 233.

*Primary Examiner*—Bruce Y. Arnold
*Assistant Examiner*—Martin Lerner
*Attorney, Agent, or Firm*—Bell, Seltzer, Park & Gibson

[57] ABSTRACT

The conformance of an unknown object to predetermined characteristics is evaluated through a characteristic signature, using its transform image. The presence at an inspection station of each successive one of the objects to be inspected is detected. The inspection system includes a rotatable disk having mask apertures that move into the line of sight of a light detector. Signals produced by scanning of timing marks upon the disk reflect which one of the plurality of masks is present in the optical path, and the photodetector determines the intensity of the transform image sampled by said mask means. The signals representing these intensities, correlated to the domain from which they emanate, are collected to form a signature for the object. This signature is compared to a known signature.

21 Claims, 2 Drawing Sheets

METHOD AND APPARATUS FOR OPTICALLY EVALUATING THE CONFORMANCE OF UNKNOWN OBJECTS TO PREDETERMINED CHARACTERISTICS

This application is a continuation of U.S. patent application Ser. No. 07/137,417 filed Dec. 23, 1987, now abandoned, which is a continuation-in-part of U.S. patent application Ser. No. 920,513, filed 17 Oct. 1986 for TRANSFORM OPTICAL PROCESSING SYSTEM and now abandoned and is related to U.S. patent application Ser. No. 07/137,464, now U.S. Pat. No. 4,878,736, filed concurrently herewith for CONTROL MEANS AND METHOD FOR OPTICAL INSPECTION SYSTEM and now U.S. Pat. No. 4,878,736 issued on Nov. 7, 1989. The disclosures of the aforesaid applications are incorporated herein by reference.

FIELD OF THE INVENTION

This invention relates to an optical object inspection system, and more specifically relates to the method and apparatus by which the optical inspection system evaluates the conformance of an unknown object to predetermined characteristics. There is produced a characteristic signature of each object undergoing inspection based upon its transform image, and this characteristic signature is compared to a predetermined characteristic signature. By way of example, the transform image may be a Fourier transform image, and the characteristic signatures for the known and unknown objects may be generated using the same equipment and methods.

BACKGROUND OF THE INVENTION

Machine vision or inspection systems have become a vital component in integrated manufacturing systems. They can sort, package, and perform defect analysis without human intervention. For instance, by inspecting holes being drilled the system can determine if a drill bit is worn.

Most machine vision systems are based upon digital electronic technology that uses serial or one dimensional processing. An image is captured and stored as a matrix of electrical signals. The image is then preprocessed to enhance edges, improve contrast, and otherwise isolate the object to be recognized. A comparison function compares the enhanced image to one or more stored reference images. These preprocessing and comparison functions are typically performed by standard microelectronic, digital equipment on a bit-by-bit or vector basis. Accordingly, the techniques are typically serial and inherently one dimensional, whereas the images being processed are two dimensional. This dichotomy results in very intensive processing requirements, is particularly difficult for one dimensional digital equipment, and, even with an extraordinary amount of memory capacity and processing capability takes a relatively long time to complete. Digital processing hardware has been enhanced and the software and algorithms have been improved over prior art machine vision systems. However, these improvements have come at the expense of additional system complexity, system costs and programming complexity, and still suffer from the inherent limitations of serial processing.

In some systems, the image to be processed is converted into a Fourier or other transform. The Fourier transform presents information about the image of the object in a very useful, symmetrical pattern which represents the object in terms of its spatial frequencies. However, the calculation of a Fourier transform on a digital computer is extremely intense, and may take a computer as powerful as a Micro Vax II about a minute to complete. Even powerful and expensive state of the art array processors take a full second to merely produce the transform. In modern industrial plants, the production line rates are often a full order of magnitude faster than this.

The computational intensity and time are significantly reduced using parallel processing techniques, such as those available when the real image of the object undergoing inspection is converted to a transform image and optically processed. Following generation of the transform image it is "processed" by quantifying the light from a preselected number of spatial domains or segments of the transform image. These quantities are then electronically processed to provide an abbreviated or composite characteristic signature of the transform image, and thus of the object upon which it is based. In comparison to the time and expenses involved when dealing with entire transform images, the signatures may be rapidly and economically obtained and then evaluated to determine whether the object does or does not conform to preselected standards.

Although possessing the above-noted benefits, an inspection system of the foregoing type must include signature-generating means, in addition to the other system components such as means for generating electrical signal data representative of the appearance of each inspected object, means for receiving such signal data and producing a visual image of each object represented thereby, and means for producing a transform image of the object from the aforesaid visual image. By producing one or more characteristic signatures derived from a known sample of all good or all bad objects, one can automatically generate a signature representing a predetermined range of acceptable or good items, or carefully pinpoint and classify the nature of the problems that result in reject items. This requires, as a prerequisite, a simple, fast and reliable method and apparatus for providing the "signature" or data vector representing the predetermined characteristics against which the unknown objects will be tested.

SUMMARY OF THE INVENTION

With the foregoing in mind, the present invention provides an improved method and means for optically evaluating the conformance of unknown objects to predetermined charactertistics and includes the steps of generating a transform image of a known object; sampling the light from different spatial domains of the transform image and generating signal data representative of the different domains; collecting the signal data and collectively defining and storing a characteristic electric signature vector representing the transform image of the known object; generating an optical transform of an unknown object; sampling light from different spatial domains of the transform image of the unknown object and generating signal data representative of the different domains; collecting the signal data and collectively defining a characteristic electric signature vector representing a transform image of the unknown object; and comparing the electric signature vectors presentating the unknown and known objects and determining whether the signature vector of the unknown object conforms to the boundaries of the signature vector for the known object. The method includes sampling the light intensity as one method of characterizing the different domains of the transform image, generating optical transform images of a variety of known objects to define a range of values for each domain of the transform optical image, and determining statistical variations among certain ones of the sampled light quantities from the different spatial domains. The apparatus includes first imaging means for generating electrical signal data representative of the appearance of each inspected object, second imaging means for receiving the signal data and generating a visual image of the object, third imaging means for receiving and generating a transform image from the visual image of the object, and signature generating means for sampling light from different spatial domains of the transform image and generating electrical signal data representative thereof and collectively defining a characteristic signature of the inspected object. A control means controls and coordinates the operation of the foregoing system components so as to permit both quite rapid and highly accurate inspection of the objects.

In a preferred embodiment of the apparatus for implementing the invention, the signature generating means of the inspection system includes movable mask means for obtaining samples of light from different spatial domains of the transform image, a system control means synchronizes the operation of other system components and the movement of the mask means, and a computer collects the data representing the intensity of the light from the different spatial domains of the transform image, assembles the data to define a characteristic electric signature vector representing the transform image of the known object, and compares this formed signature vector to a corresponding signature vector representing the transform image of the unknown object.

The first imaging means of the inspection system may and preferably does include sensing means for sensing the presence of an object at a preselected inspection location, stroboscopic lighting means for illuminating each object at such location, and video camera or similar means for generating electrical signals representative of the appearance of an object present at such location. The control means initiates operation of the stroboscopic lighting means and thereafter ensuing transmission of the desired signal data from the camera means only after it has verified that the object in question is within the field of view of the camera means, and the latter has completed its transmission of signal data representative of the appearance of a preceding object at the inspection location. The control means preferably further delays operation of the light-sampling and other components of the signature generating means of the system until the optical real and transform images of the object undergoing inspection are of an optimal quality.

When the optimal transform image of the object has been generated, the light sampling or mask means isolates different spatial domains of the transform image and a photodetector generates an electrical signal representative of the light intensity in each of the different domains. The electrical signal data is stored corresponding to each domain and this correlated data collectively defines an electric signature vector representing the transform image of the known object. This same technique is used for collecting the signature of a known object, whether it be a "good" or "bad" object, and the signature of an unknown object. The signature vectors may be compared, after being preprocessed as necessary or desirable, to ultimately determine whether the unknown object conforms to the predetermined characteristics of the known object.

Thus, the method is more than merely a means of determining conformance of an unknown object to a predetermined signature, but also, a method for organizing and generating the signature in the first place. The signature allows the global characterization of the complete appearance of the object.

Once the signatures have been collected to form a complete characterization of the good objects, anything that does not have an acceptable signature can be rejected. This makes possible training during on-line production time. The method contemplates gathering many signatures, clustering and analyzing the signatures, forming a generalization of a correct signature, and setting meaningful thresholds between good and bad.

DESCRIPTION OF THE DRAWINGS

Other features of the invention will be apparent from the following description of an illustrative embodiment thereof, which should be read in conjunction with the accompanying drawings, in which.

DESCRIPTION OF THE PREFERRED EMBODIMENT

Figure 1:
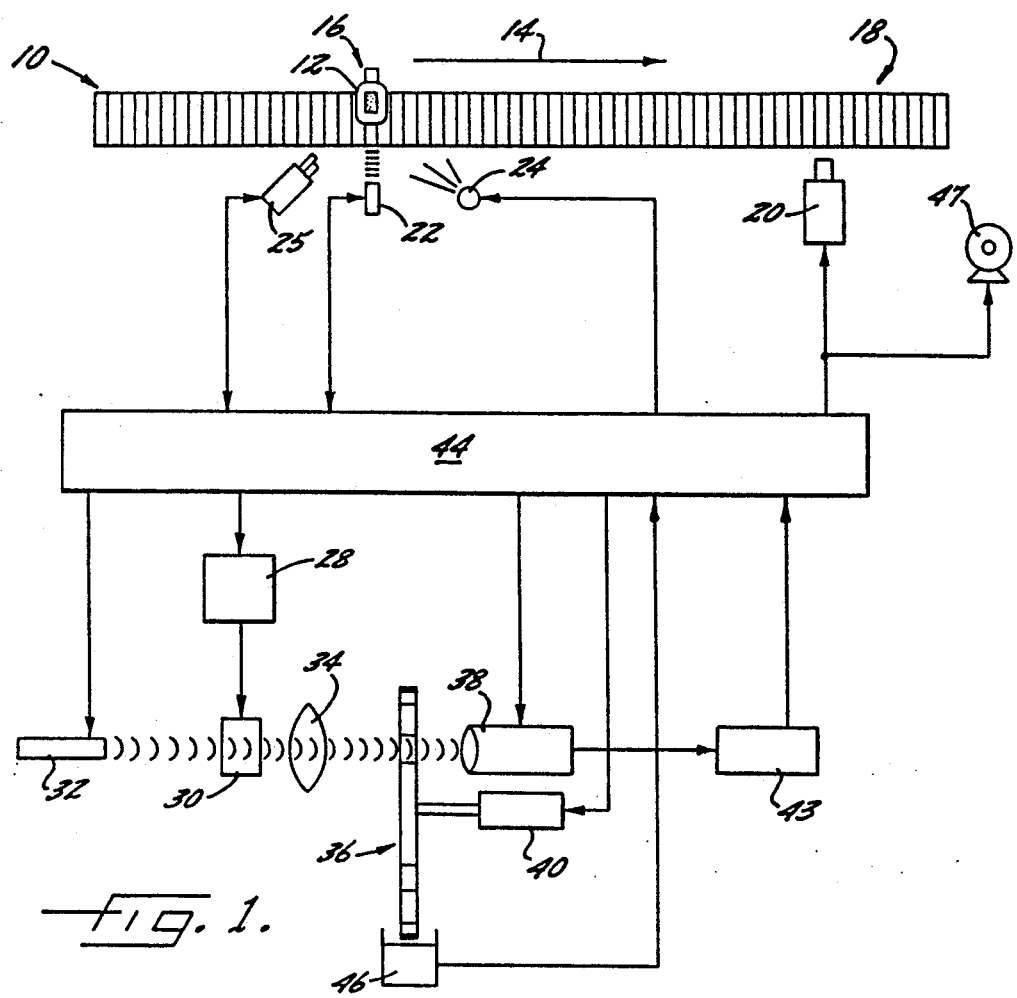
FIG. 1 is a schematic and diagrammatic view of operational and control components of an optical object inspection system in accordance with the invention.

Referring more particularly to the drawings, the numeral 10 in FIG. 1 designates conveyor means for sequentially conducting objects 12, only one of which is shown, in the direction of the arrow 14 along a path of travel extending past an "upstream" object inspection station 16 and a "downstream" object reject station 18. Objects 12 can and normally would be transported by conveyor 10 at a relatively high speed, such as 15 objects per second, and might be packaged, canned, bottled or other items intended to be of a generally uniform or standardized type. To ensure that objects 12 meet preestablished standards of uniformity, each object is automatically inspected as it reaches inspection station 16. Those objects 12 that fail the inspection are moved laterally from conveyor 10 at reject station 18 by a pusher mechanism 20. The "good" objects that pass the inspection are conducted by conveyor 10 past station 18 to a shipping or other desired location (not shown).

The system for inspecting objects 12 includes first imaging means for producing electrical signal data representative of the appearance of each object arriving at inspection station 16, second imaging means for receiving the aforesaid electrical signal data and producing a visual image of the object, third imaging means for producing a transform image of the object from the aforesaid visual image, signature generating means for sampling light from a limited number of different spatial domains of the transform image and generating therefrom electrical signal data defining a characteristic signature or summary of the transform image and thus of the inspected object, and control means for automatically correlating and controlling operation of the foregoing components.

More specifically with respect to the foregoing components, the first imaging means includes sensing means 22, such as a photoelectric or sonic type object detector, for sensing and signalling the arrival of each object 12 at inspection station 16; stroboscopic lighting means 24 for, when actuated, briefly illuminating the object at the inspection station; and video camera means 25 for capturing the real image of the illuminated object at the inspection station, and producing electrical signal data representative of the real image of the object.

The second imaging means of the inspection system includes frame buffer means 28, and spatial light modulator ("SLM") means 30 which may be and preferably is a liquid crystal display device. Frame buffer 28 receives the signal data essentially in real time as it is generated by camera 25, and retransmits the data to SLM 30 at a predetermined time, causing the SLM to produce a high-quality visual image of the inspected object 12. The frame buffer is typically a fast access random access memory device that stores each line of real image data as it is generated. When all of the real image data has been stored, i.e. the last horizontal trace has been generated and stored, all of the data is transmitted to the spatial light modulator. And, when caused to do so by the control means of the inspection system, frame buffer 28 also causes rapid quenching of the image generated by SLM 30.

The third imaging means of the inspection system includes a laser 32 or other means for producing a coherent beam of light that passes through SLM 30 and defines the optical axis of the system. In passing through the SLM the real image generated by the SLM is impressed on the beam of light. The third imaging means further includes lens means 34 that receives the now modulated light beam carrying the real image of the object 12, and converts that image into a Fourier or other transform image of the inspected object.

Figure 2:
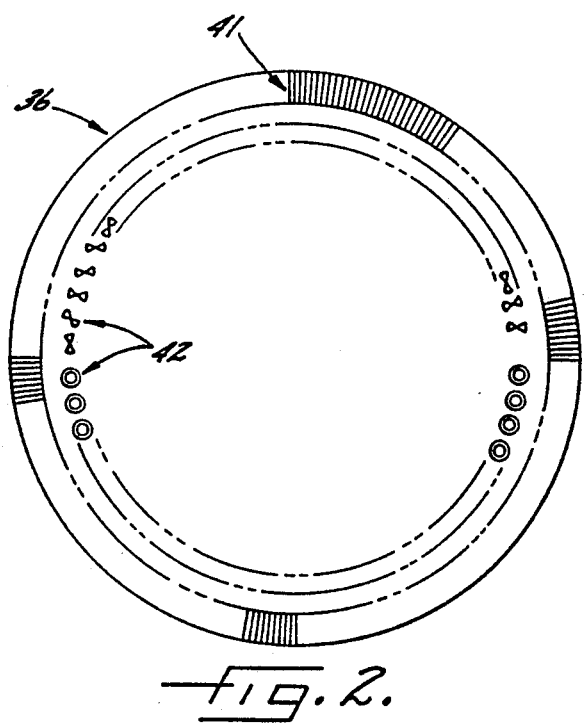
FIG. 2 is an enlarged side elevational view of a rotatable mask component of the system.

The sampling and signature generating means of the apparatus include movable mask means, illustratively in the form of a rotatable disc 36, and light detecting and measuring means such as a photodetector device 38. Disc 36 is adapted to be rotated at a constant speed about its central axis by a servo motor 40, and is also shown in FIG. 2 of the drawings. Disc 36 has a circular array of wedge and ring shaped masks 42 of differing orientations, configurations and/or sizes. Each mask may represent a different spatial domain or segment of the transform image, but together they represent a composite or mosaic of entire image.

As disc 36 undergoes rotation about its central axis, successive ones of the masks 42 move into alignment with the optical path or line of sight between photodetector device 38 and lens means 34. The light transmitted to photodetector device 38 via different ones of disc apertures 42 therefore is from different spatial domains of the Fourier transform image generated by lens 34. The light thus received by photodiode device 38 from a preselected limited number of different spatial domains of the transform image is converted by device 34 into electrical data signals. Such signals are individually representative of the intensity of the light received by detector device 38 from respective ones of the sampled spatial domains of the transform image. Collectively they represent a characteristic signature of the transform image and thus of the object 12 at inspection station 16. By way of example, the disc 36 includes thirty two masks, divided into two sets of sixteen. One set of sixteen includes 16 wedge or "bow tie" shaped masks, and the other set includes 16 ring or donut shaped masks. Each of the wedge shaped masks is 180/16 = 11.25 arc degrees wide and is oriented at a different arc degree angle in complementary 11.25 arc degree segments. Together the 16 wedge shaped masks form a composite of the entire image area. Similarly, each of the donut shaped masks has a different radius so that together they also form a composite of the entire image area.

The disk also includes timing marks 41 at its perimeter. The timing marks may be masks and may be optically detected using one of several known techniques or sensing means 46 to determine the speed and precise angular orientation of the disc.

The signal data generated by device 38 representing the intensity of the transform image domains defined by each of the masks 42 is processed by conventions signal processing means 43. This may include such things as a current-to-voltage converter, a sample and hold circuit, an analog-to-digital converter, and a buffer means.

Figure 3:
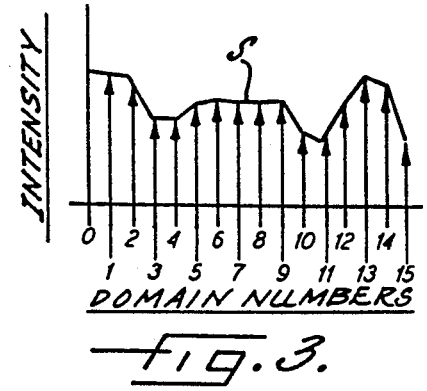
FIG. 3 is a map or graph of the intensity of the transform image in each of sixteen domains, representing the signature of the object being inspected.

The output data from signal processing means 43 is received by a computer, which is also part of the control means 44 of the inspection system. The data received by the computer represents the light intensity for each domain of the transform image. By mapping the intensity for each domain, as shown in FIG. 3, a unique signature line S is generated for each object inspected. The computer contains data, which may be based upon prior analysis of the characteristic signatures of a number of "good" objects previously inspected by the system, that is used to determine from its characteristic signature data whether the object 12 currently undergoing inspection falls within the acceptable limits defining a "good" or "bad" category. In the event of a "bad" category determination, controller 44 directs a control signal to pusher mechanism 20 causing the object 12 in question to be displaced by the pusher mechanism from conveyor 10 when the object reaches reject station 18. Controller 44 may also maintain a record of the number of bad objects detected during a particular time period and actuate an alarm 47 if such number reaches a predetermined limit.

In addition to the foregoing functions, controller 44 automatically controls and coordinates the operation of various of the components of each of the three imaging means and the signature generating means of the inspection system. At the outset of a typical cycle of operation of the inspection system, the arrival of an object 12 at inspection station 16 and within the field of view of camera 25 is detected by detector 22 and reported to controller 44. Controller 44 continuously monitors the operation of camera 25, display device or SLM 28 and photodetector 38. If the condition of the latter components is suitable for commencement of a cycle of operation of the inspection system, the controller 44 initiates the same upon receipt of the signal from detector 22. If one or more of the aforesaid components is not in suitable condition, initiation of the inspection cycle is delayed until it or they are in proper condition.

When the object is in the proper position, controller 44 effects actuation of strobe light 24 and transmission from camera 25 to frame buffer 28 of signal data representative of the real image of the inspected object 12. Such data is received and stored by frame buffer 28, and when the entire real image has been stored it is then transmitted to the liquid crystal SLM 30. The SLM may thereafter be refreshed by the frame buffer for a predetermined time period as necessary and specified by controller 44 and commensurate with the response time of the SLM 30 employed in the inspection system.

The visual image produced by SLM 30, and then impressed upon the light beam generated by laser 32, is converted by lens means 34 into a transform image. The different spatial domains are viewed by photodetector 38 as different ones of the mask apertures 42 of disk 36 move, as the disk rotates, into the optical path of the detector 38.

Constant-speed rotation of disk 36 by its servo motor 40 is initiated by controller 44 when the inspection system is first placed into operation, and is thereafter monitored by the controller. The timing marks 41 present upon the disk 36 are continuously scanned by sensing means 46 (FIG. 1), of a tachometer type, associated with the disk. The output of tachometer 46 continuously produces a signal representative of the uniform rate of rotation of the disk. This signal also permits identification by controller 44 of the instantaneous rotative position of respective ones of the disc apertures 42 relative to the optical path between photodetector 38 and the transform image. The tachometer signal is utilized by the controller 44 to correlate the light intensity signal data generated by photodetector 38 to each successive mask aperture 42 (i.e. transform image spatial domain) of the disk. Such correlation is necessary for proper identification and subsequent comparison, by the computer component of controller 44, of the characteristic signature signal data generated during each inspection cycle with the characteristic signature signal data stored in the computer and relating to "good" objects.

The acceptance of signals from the photodetector 38 during each inspection cycle is delayed until the images generated by devices 30, 34 are in an optimum condition. The duration of the delay depends upon the response time of the particular device 30 employed in the inspection system, as well as possibly other factors. In one particular utilization of the system wherein the inspection cycle time for each object was 66 milliseconds, the transform image was most stable during the last 24 milliseconds of each cycle, and the characteristic signature of the image was obtained during such terminal period. It is of course understood that during such period the generation and/or transmission of signal data by detector 38 is permitted by controller 44 only when successive ones of the mask apertures 42 are aligned with the optical path between the transform image and device 38.

The signatures which represent the distribution of spatial frequencies in the transform image are collected and stored in a sample file. The light intensity for each domain of the transform image represents a feature of the signature. The line drawn between the intensity points for each domain, as illustrated in FIG. 3, represents the signature S itself. The domains are numbered on the horizontal axis in FIG. 3 for reference, with relative intensity indicated on the vertical axis. Fewer or more domains may be used, depending on the application of the invention. The corresponding features of all signatures in the sample file are averaged to form a composite signature for each sample file. The difference between the highest and lowest intensities for each domain or feature of the signature represents the range within which a domain intensity or feature must fall to be acceptable.

Figure 4:
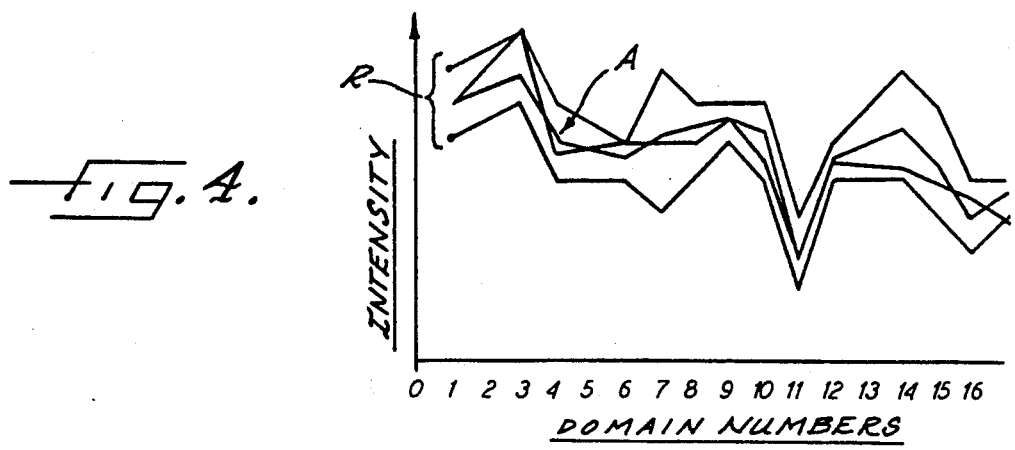
FIG. 4 is a typical map or graph of the signatures of numerous objects with the multiple signatures being superimposed one on the other to define acceptable ranges for each of the 16 domains.

Referring to FIG. 4, the average signature for a group of similar products is designated by reference numeral A and the acceptable range of intensity for domains 1 is represented by reference numeral R. The domains are numbered on the horizontal axis in FIG. 4 for reference, with relative intensity indicated on the vertical axis. Fewer or more domains may be used, depending on the application of the invention. The signature may be comprised of selected subsets of data from the sampled transform image. For instance, a "shape" signature typically represents the orientations of the transform image frequencies or the shape of the image as generated by the wedge shaped masks. A "texture" signature represents the frequency distribution of the transform image or its texture as generated by the ring shaped masks.

A further technique utilizes an "offset" which causes the apparatus to subtract any system background signature that may be included within a given signature. Removal of the background is not necessary to effective operation of the system because the signatures for the known and unknown objects, assuming they are generated using the same apparatus, will both include the same background components. Since they are discriminated based upon the relative differences between the two, background that is present effectively cancels itself out. To generate the offset signature, a blank piece of paper is used as an object and has a signature generally represented by a straight line.

To evaluate the conformance of unknown objects to a good object set, a group of good objects is passed in front of the camera and their signatures are recorded to generate a sample or average signature vector representing the composite transform image of the good objects. Under certain circumstances it may be desirable to generate a sample of known objects comprised entirely of rejects so that the nature of the reject can be identified.

Having collected a plurality of signatures for known objects, statistical evaluations may be generated to evaluate the validity of the collected data or the significance of variations for one or more of the domains. This is typically done in terms of distance metrics. Another technique is to generate a covariance matrix, which collects numerical data reflecting the manner in which the characteristics in different domains vary in the same direction and magnitude.

As an example of a distance metric, the Euclidian distance for a signature is calculated by adding the squared differences of each features' value and its mean value for all the features of signatures in a sample file and deriving the square root of this sum. The Euclidian distance accumulates separation for every feature of a signature. While there may not be much separation between one feature and another, total separation of signatures from one sample file to another can be substantial and significant. Another evaluation that is useful is to determine the largest separation between features of the signatures. This metric is easy to compute and is not sensitive to cumulative differences among features. An average is calculated which represents the average of all of the signatures in the sample file. A standard deviation is calculated which is a measure of the variation from the mean among the items in the sample. The larger this number the greater the difference among the items in the sample file, whether they are good or reject objects. Another measure of variation is the most different object measurement. It reflects how far the best reject item in the sample differs from the mean. The larger this number the greater the difference between the mean or average of all of the signatures in the file and the signature which is most different from the mean. Other techniques include the Chebychef Metric, the Fukanaga-Koontz algorithm, the Foley-Solmon algorithm, and Fisher's Linear Discriminant.

To make accept/reject decisions the electric signature vectors representing the unknown and known objects are compared to a threshold between the signature representing the good objects and a signature representing the reject objects. If a signature falls outside of the ranges established for the different domains of the good objects, a broader range may be established by defining a threshold which is midway between the range of signatures for good samples and the range of signatures for rejected samples. This provides a larger measure of acceptance for good objects, yet ensures a minimum distance from those signatures which characterize reject objects. The threshold may be placed automatically or manually, as necessary or desirable. Through these procedures it can sense a clustering of signatures at different points in the metric and place the thresholds automatically to distinguish between the segments of the metric represented by the clustering of the signatures. The larger the distance or window between the signatures representing the good objects and the rejected objects, the higher the probability for accurate discrimination between good and rejected objects during product inspection.

Figure 5:
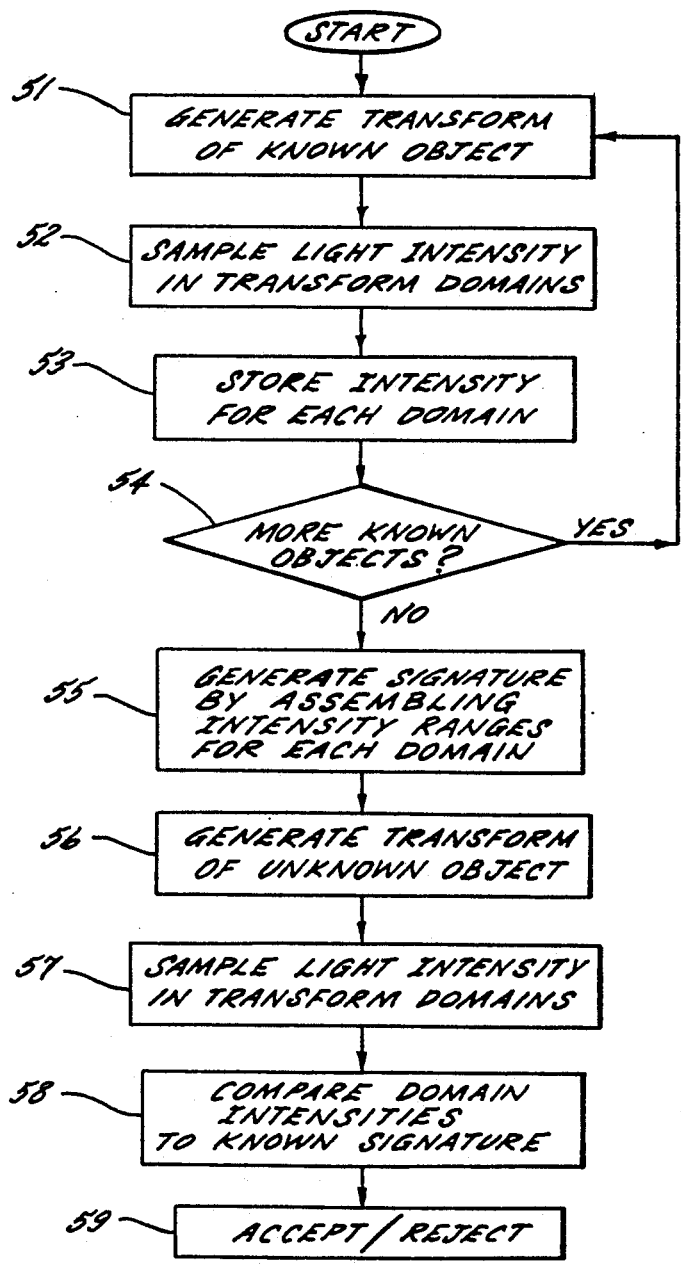
FIG. 5 is a schematic flow chart illustrating the method of operation of the present invention using the apparatus disclosed herein and in the parent and related applications.

Referring to FIG. 5, the sequence of steps 51-54 represent the generation of the optical transform image of a known object, sampling of the light intensity in the transform domains for each of the known objects, and the storing of the intensity for each domain of each of the sampled objects. This loop continues for the entire group of known objects. After the electrical signal data representing the intensity for each domain of each known object has been stored, they are collected to define a characteristic electric signature vector representing the transform image of the known object. This signature vector is typically a compilation of all of the intensities in each domain, and the intensities may be used to establish an average signature vector or a range of values that represent acceptable characteristics of the Fourier transform for the various domains of the object. This is represented by box 55 in FIG. 5.

Steps 56 and 57 represent the generation of an optical transform image of an unknown object and the sampling of light from the different spatial domains of the transform image of the unknown object in the same manner, as was done in connection with the known objects. Electrical signal data representative of the sampled light from each of the different domains thereof is collected to define a characteristic electric signature vector representing the transform image of the unknown object. The electric signature vector representing the transform image of the unknown object is compared, domain by domain, with the electric signature vector representing the transform image of the known object, and may be implemented using a neural network or standard computer processing techniques. Depending upon the ultimate results desired, this comparison may represent the degree of conformance to the average signature, the number of domains for which the transform of the unknown object matches the average signature for the known object, the number of domains for which the signature of the unknown object falls within the acceptable ranges for the domains of the transform image of the known object, etc. Statistical evaluations of the number of good versus reject objects, as well as the highest degree of variation present, may be performed. Depending upon the degree of correlation between the signature vector for the known and unknown objects, a decision representing the acceptance or rejectance of the inspected object is formulated and an electrical signal representative thereof is transmitted to a downstream station to collect or detour the unknown object.

While a preferred embodiment of the invention has been specifically shown and described, this was for purposes of illustration only, and not for purposes of limitation, the scope of the invention being in accordance with the following claims.

That which is claimed is:

1. A method for optically evaluating the conformance of an unknown object to a standard comprising the steps of:
   a) generating a plurality of optical transform images of a corresponding plurality of samples of a known object;
   b) sampling light from different angular and radial components of the spatial domains of the plurality of transform images of the corresponding plurality of samples of the known object and generating electrical signal data representative of the different domains thereof independent of any electrical signal generated in response to the detection of the real image of the plurality of samples of the known object;
   c) collecting the electrical signal data representing the different angular and radial components of the spatial domains of the plurality of transform images of the corresponding plurality of samples of the known object and collectively defining and storing a composite electric signature vector representing the transform images of the plurality of samples of the known object;
   d) generating an optical transform image of an unknown object;
   e) sampling light from different angular and radial components of the spatial domains of the transform image of the unknown object and generating electrical signal data representative of the different domains thereof independent of any electrical signal generated in response to the detection of the real image of the known object;
   f) collecting the electrical signal data representing the different angular and radial components of the spatial domains of the transform image of the unknown object and collectively defining a characteristic electric signature vector representing the transform image of the unknown object; and
   g) comparing the electric signature vectors representing the transform images of the unknown object and the plurality of samples of the known object and determining whether the signature vector of the unknown object conforms to the composite signature vector for the known plurality of samples of the object, and thus determining whether the unknown object qualifies as an acceptable object.

2. The method of claim 1 wherein the steps of generating transform optical images comprises generating optical transform images using light reflected from a representation of an object.

3. The method of claim 1 wherein the steps of sampling light and generating electrical signal data representing a transform image of an object comprises sampling light from multiple angular and radial components of the spatial domains of the transform image and generating electrical signals representative of the intensity of the light in each of the different domains sampled.

4. The method of claim 1 wherein the step of collecting, for the plurality of samples of the known object, the electrical signal data and defining and storing a composite signature vector comprises correlating the electrical signal data to the angular and radial components of the spatial domain it represents and storing the correlated signal data in a predetermined order according to the domain it represents.

5. The method of claim 1 wherein the step of sampling light from different angular and radial components of the spatial domains of the transform image of the unknown object comprises sampling light from different angular and radial components of the spatial domains of the transform image of the unknown object that correspond to the angular and radial components of the spatial domains sampled from the transform image of the known object.

6. The method of claim 1 wherein the step of collecting, for the unknown object, the electrical signal data and defining a signature vector comprises collecting the electrical signal data and defining a signature vector in the same manner as was done for the known object.

7. The method of claim 1 wherein the step of collecting, for the plurality of samples of the known object, the electrical signal data and defining and storing a composite signature vector comprises defining and storing a signature vector including predetermined acceptable data ranged derived from the collected electrical signal data.

8. The method of claim 1 further including the step of generating electrical data signals representative of the difference between the signature vectors of a plurality of samples of the known object.

9. The method of claim 1 wherein the step of collectively defining a signature vector further comprises generating statistical data representing variations among predetermined ones of the collected electrical signal data and deriving an optimum value therefor based upon the determined variation.

10. The method of claim 9 wherein the step of generating statistical data comprises determining the Euclidian distance for the signal data in different spatial domains of the transform image of the objects.

11. The method of claim 9 wherein the step of generating statistical data comprises determining the largest separation between features in different spatial domains of the transform image of the objects.

12. The method of claim 1 wherein the step of defining and storing a composite electrical signature vector representing the transform images for the plurality of samples of the known object comprises defining and storing a single composite signature vector representing a range of acceptable signal data values of the angular and radial components of the spatial domain on the transform image, with the range being defined between the highest and lowest signal data for the spatial domain for the plurality of samples of a known object.

13. Means for optically evaluating the conformance of an unknown object to a standard comprising:
  a) means for generating a plurality of optical transform images of a corresponding plurality of samples of an object;
  b) means for sampling light from different angular and radial components of the spatial domains of the plurality of transform images of the corresponding plurality of samples of the object and generating electrical signal data representative of the different domains thereof independent of any electrical signal generated in response to the detection of the real image of the plurality of samples of the known object;
  c) means for collecting the electrical signal data representing the different angular and radial components of the spatial domains of the plurality of transform images of the corresponding plurality of samples of the object and collectively defining and storing a composite electric signature vector representing the transform images of the known object;
  d) means for comparing the electric signature vectors representing the transform images of unknown object and the plurality of samples of the known object and determining whether the signature vector of the unknown object conforms to the composite signature vector for the plurality of samples of the known object, and thus determining whether the unknown object qualifies as an acceptable object.

14. The apparatus of claim 13 wherein the means for generating transform optical images comprises means for generating optical transform images using light reflected from a representation of an object.

15. The apparatus of claim 13 wherein the means for sampling light and generating electrical signal data representing a transform image of an object comprises means for sampling light from multiple angular and radial components of the spatial domains of the transform image and generating electrical signals representative of the intensity of the light in each of the different domains sampled.

16. The apparatus of claim 13 wherein the means for collecting the electrical signal data and defining and storing a signature vector comprises means for correlating the electrical signal data to the angular and radial compoents of the spatial domain it represents and storing the correlated signal data in a predetermined order according to the domain it represents.

17. The apparatus of claim 13 wherein the means for sampling light from different angular and radial components of the spatial domains of the transform image of the unknown object comprises means for sampling light from different angular and radial components of the spatial domains of the transform image of the unknown object that correspond to the angular and radial components of the spatial domains sampled from the transform image of the known object.

18. The apparatus of claim 13 wherein the means for collecting the electrical signal data and defining and storing a signature vector comprises means for defining and storing a signature vector including any predetermined acceptable data ranged derived from the collected electrical signal data.

19. The apparatus of claim 13 further including means for generating electrical data signals representative of the differences between the signature vectors of a plurality of samples of the known objects.

20. The apparatus of claim 13 wherein the means for collectively defining a signature vector further comprises means for generating statistical data representing variations among predetermined ones of the collected electrical signal data and deriving an optimum value therefor based upon the determined variation.

21. The apparatus of claim 13 wherein the means for defining and storing a signature vector representing a composite transform image for the plurality of samples of the known object comprises means for defining and storing a single signature vector representing a range of acceptable signal data values for the angular and radial components of the spatial domain of the transform image, with the range being defined between the highest and lowest signal data for the spatial domain.

* * * * *

UNITED STATES PATENT AND TRADEMARK OFFICE
CERTIFICATE OF CORRECTION

PATENT NO. : 5,078,501
DATED : January 7, 1992
INVENTOR(S) : Hekker et al

Page 1 of 2

It is certified that error appears in the above-indentified patent and that said Letters Patent is hereby corrected as shown below:

On the title page,

Item [73], Assignee "E. I. Du Pont de Nemours and Company" should be --E. I. du Pont de Nemours and Company--

Item [56] References Cited: Column 2, the following patents should be added:

| | | |
|---|---|---|
| 3,771,129 | 11/1973 | McMahon |
| 4,115,801 | 9/1978 | Salmen et al. |

Item [56] References Cited: Column 2

| | | |
|---|---|---|
| 4,174,179 | 11/1979 | "Tsuchudi et al." should be --Tschudi et al.-- |

UNITED STATES PATENT AND TRADEMARK OFFICE
CERTIFICATE OF CORRECTION

PATENT NO. : 5,078,501
DATED : January 7, 1992
INVENTOR(S) : Hekker et al.

It is certified that error appears in the above-indentified patent and that said Letters Patent is hereby corrected as shown below:

```
   Item [56]  References Cited:   Column 1

4,556,985      12/1985          "Hogno" should be
                                      -- Hongo--

Column 11, line 39 (Claim 7), "ranged" should be --
ranges--.

Column 12, line 63 (Claim 18), "ranged" should be --
ranges--.
```

Signed and Sealed this

Twenty-fourth Day of August, 1993

*Attest:*

BRUCE LEHMAN

*Attesting Officer*   *Commissioner of Patents and Trademarks*